(12) United States Patent
Paul et al.

(10) Patent No.: US 6,332,540 B1
(45) Date of Patent: Dec. 25, 2001

(54) DEVICE FOR ISOLATING SMALL POLYMERIC BEADS FROM A SUSPENSION OF SUCH BEADS

(75) Inventors: Frank Paul, Ware; Philip John James, Welwyn Garden City; Richard C Payne, Harpenden, all of (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/402,686

(22) PCT Filed: Apr. 8, 1998

(86) PCT No.: PCT/GB98/01039

§ 371 Date: Dec. 2, 1999

§ 102(e) Date: Dec. 2, 1999

(87) PCT Pub. No.: WO98/45683

PCT Pub. Date: Oct. 15, 1998

(30) Foreign Application Priority Data

Apr. 8, 1997 (GB) .................................................. 9707096

(51) Int. Cl.[7] .................................................. B07C 5/02
(52) U.S. Cl. ............................................. 209/3.1; 209/552
(58) Field of Search ........................... 209/3.1, 3.2, 10, 209/552, 577, 579, 587; 406/86–88, 92, 94

(56) References Cited

U.S. PATENT DOCUMENTS

| 3,826,364 | * | 7/1974 | Bonner et al. ........................... 209/3 |
| 3,827,555 | | 8/1974 | Kamentsky et al. . |
| 3,984,307 | | 10/1976 | Kamentsky et al. . |
| 4,756,427 | * | 7/1988 | Gohde et al. ........................ 209/3.1 |
| 4,870,143 | * | 9/1989 | Hasiguchi et al. ..................... 526/70 |
| 5,914,262 | * | 6/1999 | MacMichael et al. ............... 435/243 |

FOREIGN PATENT DOCUMENTS

| WO 90/11832 | 10/1990 | (WO). |
| WO 91/15750 | 10/1991 | (WO). |
| WO 94/15193 | 7/1994 | (WO). |
| WO 94/28119 | 12/1994 | (WO). |
| WO 97/45644 | 12/1997 | (WO). |

* cited by examiner

Primary Examiner—Christopher P. Ellis
Assistant Examiner—Joseph Rodriguez
(74) Attorney, Agent, or Firm—Nora Stein-Fernandez; Stephen Venetianer; Charles M. Kinzig

(57) ABSTRACT

A device for separating polymeric beads from a suspension of such beads comprising a flow cell through which the suspension of beads flows, and a radiation source which the stream of beads crosses. A detector detects the presence of a bead in the flow cell and control means directs the bead to a bead outlet channel.

32 Claims, 4 Drawing Sheets

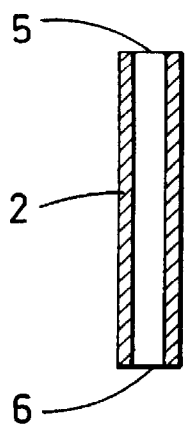
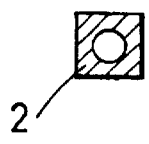
Fig. 3A
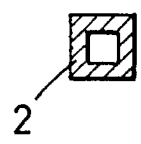
Fig. 3B
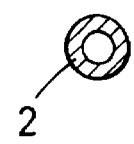
Fig. 3C
Fig. 3
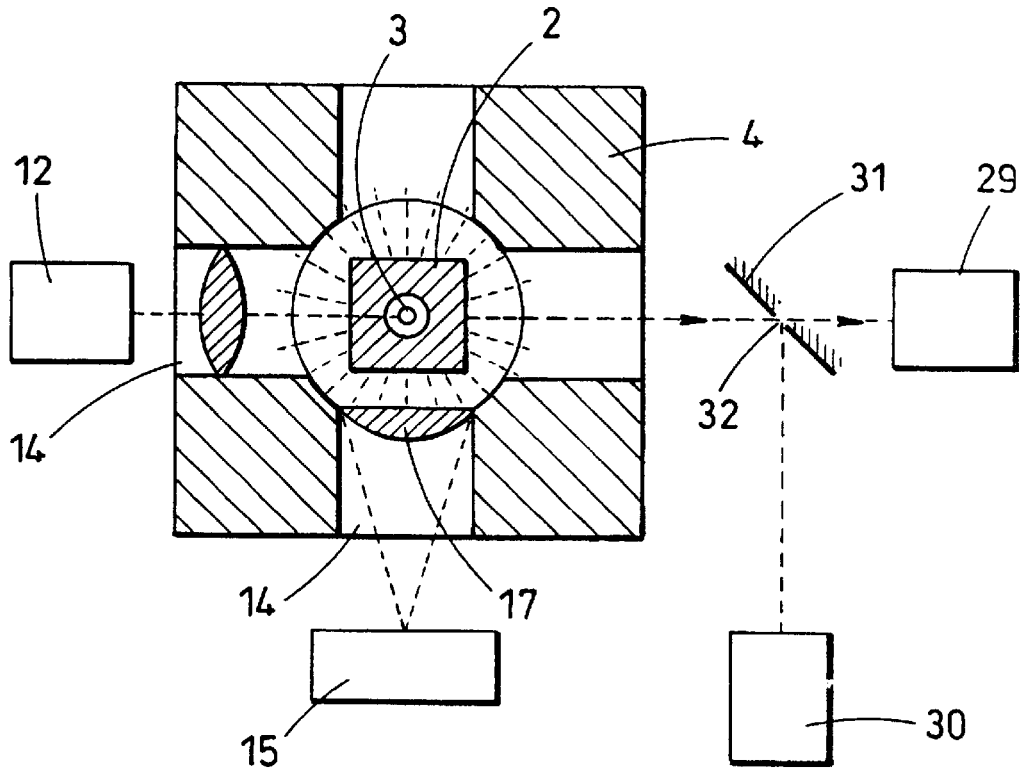
Fig. 4

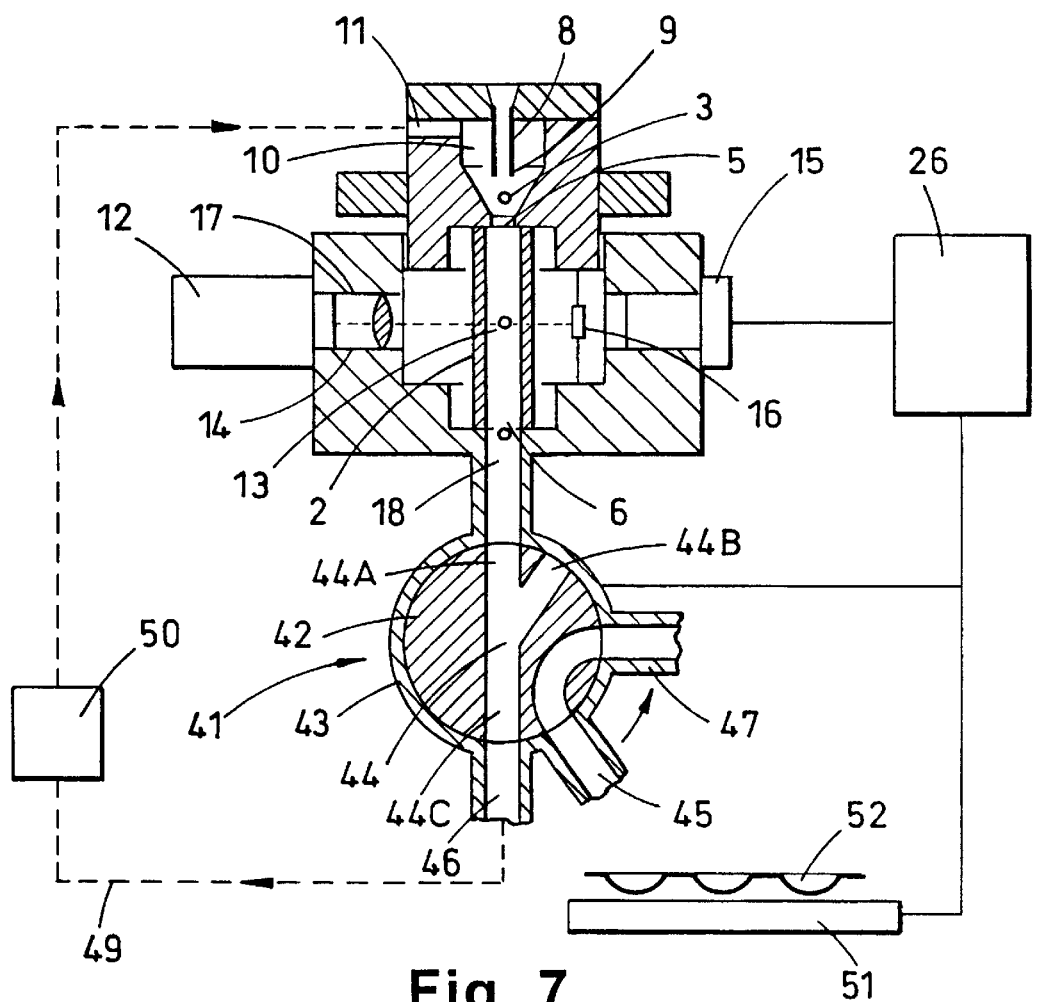
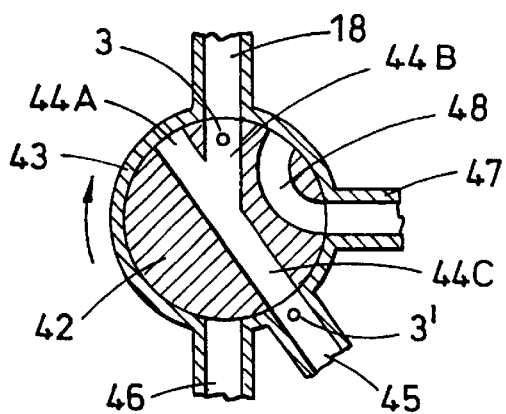
Fig. 8
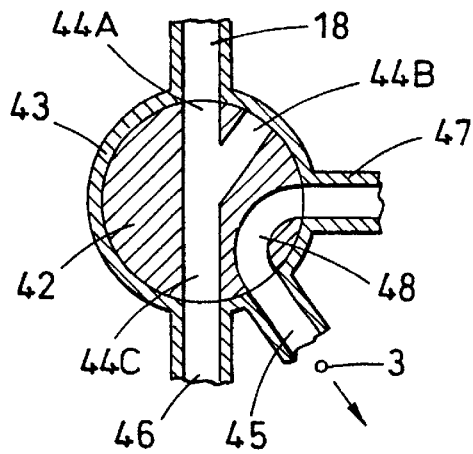
Fig. 9

DEVICE FOR ISOLATING SMALL POLYMERIC BEADS FROM A SUSPENSION OF SUCH BEADS

FIELD OF THE INVENTION

This invention relates to a novel device suitable for separating polymeric beads from a suspension of a plurality of such beads in a fluid.

BACKGROUND OF THE INVENTION

In chemistry and biochemistry chemical reactions are frequently performed on the surface of small polymeric resin beads of a diameter range 50–600 microns, typically 250–300 microns in diameter. For example an active substance may be chemically absorbed onto such a bead, e.g. on its surface and/or into the body of the bead, the treated bead may then be exposed to further active substances or labels such as fluorescence labels, and the occurrence of an interaction between the various active substances and/or labels can be detected by monitoring the bead. This technique is particularly useful in biological sciences where only minute amounts of such active substances may be available, and in the investigation of combinatorial chemistry libraries.

In such techniques it is usually necessary to transfer individual beads from a source containing many such beads, e.g. a suspension (which term as used herein includes inter alia a slurry) of the beads in a liquid, into defined locations in a receptacle, for example individual vials, or individual wells in a microtitre plate.

A number of problems hinder such transfer. The small size of the beads makes them difficult to manipulate. It is difficult to transfer beads using present techniques without at the same time transferring a relatively large quantity of liquid. Often large numbers of beads are involved, and present methods of transferring beads suffer from the problems inherent in handling large numbers of small beads. At present either manual methods, e.g. picking out single beads by hand, or excessively complex devices are used.

One device for automatically separating beads from a suspension of a plurality of beads in suspension in a fluid is disclosed in WO 94/28119, which is a large scale device, primarily intended for use with beads of diameter ca. 3 mm, and for separating beads containing encapsulated biomass from empty beads. Devices for automatically separating smaller particles, e.g. cells suspended in a fluid, are disclosed in U.S. Pat. No. 4,756,427, U.S. Pat. No. 5,030,002 and U.S. Pat. No. 4,175,662. It is considered unlikely that the bead sorting devices disclosed in these last mentioned US patents could be adapted directly for use in separating the above mentioned polymeric beads used in chemical reactions. Moreover they all suffer from the disadvantage that the suspended particles remain in a substantial bulk of suspension fluid even after separation. This means that if the particles are to be delivered to a particular location, e.g. a specified well in a microtitre plate, this excess of fluid accompanies the particle to the location.

It is an object of this invention to provide a device which is more suitable for operation with smaller volumes of suspension and for the above-mentioned smaller polymeric beads. It is also an object of this invention to provide a device which can separate beads and can be used with a range of sizes of beads, i.e. not being limited to a particular size of bead.

SUMMARY OF THE INVENTION

According to this invention, a device suitable for separating polymeric beads from a suspension of a plurality of such beads in a fluid, comprises:

a flow cell through which a suspension of the beads in the fluid can flow;

the flow cell having an inlet end through which the suspension of beads may be introduced into the flow cell, such that the beads are arranged in a successive serial flow stream as they flow through the flow cell toward an exit end of the cell;

a radiation source capable of directing incident radiation into the flow cell in an incident direction such that as beads flow through the flow cell they intercept the incident radiation;

a radiation detector positioned relative to the radiation source and to the flow of beads such that a change in the radiation detected by the detector occurs as the bead intercepts the incident beam;

a bead outlet channel and a fluid outlet channel located downstream from the point where the beads intercept the incident radiation, and being in communication with the exit end;

valve means which in a first configuration directs fluid flow preferentially through the bead outlet channel rather than through the fluid outlet channel, and which in a second configuration directs fluid flow preferentially through the fluid outlet channel rather than through the bead outlet channel, so that in the first valve configuration beads are caused to flow through the bead outlet channel;

control means responsive to a signal from the radiation detector resulting from a bead intercepting the incident beam, and which directs the valve means into the first valve configuration so that a bead flows through the bead outlet channel, and after the bead is downstream of the valve means then directs the valve means into the second valve configuration.

DETAILED DESCRIPTION OF THE INVENTION

The device is preferably used for separating polymeric beads of the type used in chemical and biochemical reactions, as mentioned above, e.g. of a diameter range 50–600 microns, typically 250–300 microns, suspended in a suspension fluid which is a mobile liquid such as water or preferably an alcohol such as methanol or ethanol.

The flow cell is suitably a cell having at least part if not all of its walls transparent to the incident radiation so that the radiation source may be located outside the flow cell. If for example the incident radiation is light, then such transparent parts or the entire cell may be made of transparent materials such as plastics materials, glass, quartz etc. In some modes of operation the detector may be responsive to secondary radiation which is of a different wavelength to the incident radiation, e.g. if as discussed below the detector is responsive to a fluorescence emission, and in this case it may be necessary for at least part if not all of the walls of the cell to be transparent to the secondary radiation. The flow cell is suitably in the form of a tube of narrow internal bore, of dimensions across the direction of flow of the beads about 1.5–4 times the diameter of the beads, for example in the case of 250–300 microns diameter beads, preferably around 600–1500 microns across. Best results appear to be achieved with a narrow bore, but not so narrow that blockage is likely.

Suitably the flow cell is a transparent walled cell having the part of its wall which faces the incoming direction of the incident radiation, and/or which face the radiation detector, substantially flat and normal to this direction. Suitably therefore the flow cell may be polygonal in cross section having opposed flat faces, particularly rectangular (which term includes square) in cross section, with the flow direction along the longitudinal tube axis. Alternatively the flow cell may have the part of its wall which faces the incoming direction of the incident radiation, and/or which face the radiation detector, of a lens shape, so that such part(s) of the wall may act as a lens and may assist in guiding the incident radiation towards the flow of beads and/or toward the radiation detector.

The suspension of beads may be introduced into the inlet end from a source by any convenient means, e.g. by injection from a reservoir such as a storage vessel or a syringe, or by means of a feeder tube etc. In a reservoir it may be necessary to provide some means such as a stirrer to keep the beads in suspension, i.e. to prevent them settling. The rate at which the beads are introduced into the inlet end may be controlled by for example a controlled pump, e.g. a metering pump or syringe pump or peristaltic pump, or by means of air pressure. The device may be constructed such that multiple samples of suspensions of beads, each sample respectively initially contained in a reservoir which is connectable with the device, may be introduced into the device, either sequentially or otherwise. A carousel of such reservoirs may be provided, and such an arrangement may be conveniently automated.

In a preferred embodiment a flow of a sheath fluid, which may be the same fluid as the suspension fluid, is introduced around the flow of suspension of beads flowing through the inlet end of the flow cell, the sheath fluid flowing in the same direction as the flow of beads. Preferably the suspension fluid and sheath fluid flow through the flow cell in laminar flow, i.e. in substantially non-mixing layers of respectively the suspension fluid and the sheath fluid. Such laminar flow helps the beads to flow smoothly through the flow cell along a substantially straight path. The sheath fluid helps to even out the flow of beads and assists in achieving suitable serial separation of beads. The flow of sheath fluid may be controlled to optimise flow of beads through the flow cell.

Such a flow of sheath fluid may be achieved by a construction of the device in which, upstream of the inlet end of the flow cell, an inlet port for the suspension of beads in suspension fluid is provided, leading to an inlet conduit being of cross section comparable to the diameter of the beads and terminating in an orifice of comparable size which opens into a sheath fluid inlet chamber of wider cross section than the orifice and surrounding the orifice, at its exit end the chamber being in communication with the inlet end of the flow cell. A flow of a sheath fluid, preferably at a greater flow rate than the suspension fluid, may be introduced into the chamber, preferably upstream of the orifice, so that an outer layer of sheath fluid surrounds an inner core of suspension fluid, and the sheath and suspension fluids flow in laminar flow into and through the flow cell.

In one embodiment the sheath chamber may be in the form of a chamber which tapers from a wider upstream end toward a narrower downstream end, for example a generally conical chamber (which term includes for example pear-shaped or having a cylindrical upstream end and a conical downstream end), coaxial with the direction of flow through the flow cell, and in communication with the flow cell at its narrow end. In this embodiment the inlet conduit may enter the chamber at its wider end, suitably at an axial position, and the orifice may be at a point along the length of the chamber where the chamber is tapering, so that the flow of fluid through the sheath chamber at this point is being compressed and is accelerating. For example in a sheath chamber of conical shape the orifice may be at a point along the length of the chamber about 0.5±0.2 of the distance between the narrow end of the chamber and the point where the conical taper starts. The sheath fluid may be introduced via an inlet near or upstream of the wide end of the conical taper.

The beads are arranged in a successive serial flow stream as they flow through the flow cell, i.e. individual beads in the flow are spaced in the direction of flow by a convenient distance in the direction of flow to facilitate the operation of the device, e.g. that ensures that only one bead at a time intercepts the incident radiation, and so that there is a sufficient time interval between successive beads that individual beads in the flow are separated. The spacing of the beads may be easily determined by for example the dimensions of the device, e.g. the orifice, inlet channel and flow cell, by the rate at which the suspension is introduced into the inlet channel, and by the flow rate of the sheath fluid. In the above-described tapering sheath chamber, the accelerating fluid flow can help to increase the longitudinal separation between beads. In a flow cell with the above-mentioned dimensions, a suitable flow rate for the beads through the flow cell is between 5–75 mm sec$^{-1}$, for example ca. 10–15 mm sec$^{-1}$. Such a flow rate can easily be achieved by appropriate control of the input of sheath fluid etc., and enable operation of the device within the working limits of known pumps, detectors, valves etc.

The radiation source may for example be a light source, e.g. in the visible, infrared or ultraviolet region of the spectrum. Suitable light sources, available in small sizes and consequently convenient for a small sized device, include lasers, particularly diode lasers, and light emitting diodes ("LED's"). High brightness LED's are particularly suitable for stimulating fluorescence emission from fluorescence labeled beads. For example the label fluorescein is stimulated by light of wavelength 490 nm, and LED's are commercially available which can emit incident radiation around this wavelength.

The incident radiation is directed into the flow cell in a direction such that as beads flow through the flow cell they intercept the incident radiation. Preferably the incident direction is substantially normal to the flow direction, with the incident radiation in the form of a narrow beam which is intercepted by the flowing beads. Suitably the width of the incident beam should be wider than the bore of the flow cell to ensure that flowing beads cannot avoid the beam.

The light source may be provided with optical guides, collimators etc., filters, focusing lenses etc. to direct the incident radiation in an optimal manner into the flow cell, e.g. in the form of a narrow beam in an optimised direction and of a preferred wavelength, and suitable optical guides of this type will be apparent to those skilled in the art. Suitably the beam of incident radiation is a substantially parallel sided beam of substantially uniform intensity across its width. Suitable optical guides, for example for simplicity a single circular lens, will be apparent to those skilled in the art.

The radiation detector is positioned relative to the radiation source and to the flow of beads such that a change in the radiation detected by the detector occurs as the bead intercepts the incident beam.

For example the radiation detector may be positioned relative to the radiation source and to the flow of beads such that the detector is in line with the incident direction, but on the opposite side of the flow of beads to the radiation source. In such an arrangement a bead will pass between the radiation source and the detector. The device may be constructed and operate such that when a bead intercepts the beam of radiation it eclipses the detector such that there is a reduction in the radiation reaching the detector. However it is preferred that between the flow of beads and the detector there is a radiation obstructer of size about the same order of magnitude as the cross section of the incident beam, for example in the form of a small opaque disc, sphere or bar, such that incident radiation does not directly impinge upon the detector but instead is deflected around the obstructer into the detector. The obstructer functions by obstructing incident radiation from directly entering the detector, but if a bead passes through the beam of incident radiation, the radiation is scattered by the bead so as to bypass the obstructer and enter the detector. Consequently a higher radiation intensity is detected by the detector when a bead passes through the beam, rather than a reduced radiation intensity that would be detected if the bead merely eclipsed the beam. Such an obstructer may be adjustable to achieve optimum effectiveness. For example the obstructer may be in the form of a strip of opaque material, thin in relation to its width, which may be adjusted by rotation about its longitudinal axis so as to present a surface varying between its width and its thickness to the incident beam.

Alternatively or additionally for example a radiation detector may be positioned relative to the radiation source and to the flow of beads such that the detector is at a non-zero angle to the incident direction, for example at 90° to the incident direction. In such an arrangement it is preferred that the flow cell has two flat transparent wall regions, one facing the incident direction and the other facing the detector, e.g. a rectangular or polygonal sectioned tubular flow cell. This arrangement is suited for the detection of fluorescence emission from the beads, at an angle to the incident direction, such that incident radiation does not directly impinge upon the detector. Alternatively or additionally between a first radiation detector and the flow of beads there may be a partly transparent mirror (e.g. a mirror with an aperture) so that part of the radiation may reach the first radiation detector through the mirror, and part may be reflected by the mirror toward a second radiation detector.

For some applications there may usefully be combinations of two or more light sources and/or detectors, for example to distinguish between beads having different characteristics.

If the detector is arranged to detect fluorescence emission from the beads it may also be arranged to detect the nature of the fluorescence emission, e.g. intensity, wavelength etc., so as to provide data about the chemical nature of substances on the beads.

The radiation detector may be any convenient radiation detector capable of detecting changes in the radiation incident upon it as bead intercepts the incident beam. Convenient detectors such as photodiodes and photomultiplier tubes are commercially available.

Located downstream from the point where the beads intercept the incident radiation there is a bead outlet channel and a fluid outlet channel. The bead outlet channel may suitably be of around the same width dimensions as the flow cell, e.g. around 600–1500 microns across, and for convenience the fluid outlet channel may be of comparable dimensions. It is preferred that the exit end of the flow cell is in communication with a common outlet channel aligned in the direction of flow of the beads, and which divides at a downstream point into two or more channels, e.g. in a branched channel arrangement where the common outlet channel divides into two channels being respectively a bead outlet channel and a fluid outlet channel, such as a forked, a "T" or preferably "Y" channel arrangement. One of these channels may comprise the bead outlet channel and the other the fluid outlet channel. Alternative arrangements are of course included within the scope of the invention, for example the bead outlet channel and fluid outlet channel may lead directly out of the flow cell.

There may be one or more bead outlet channels, for example if the device not only detects beads but also distinguishes and separates them into two or more different types of bead, for example having different optical characteristics, e.g. colour, spectroscopic or fluorescence characteristics.

The valve means may be capable of restricting flow through the respective bead outlet channel and fluid outlet channel to the extent that flow through the respective channel is completely closed off. Alternatively the valve means may be capable of directing flow preferentially through the respective bead outlet channel or fluid outlet channel, for example to the extent that flow through the respective other channel is completely closed off. In the above-described arrangement where flow branches from a common outlet channel, e.g. in a branched channel arrangement, or when the bead outlet channel and fluid outlet channel lead directly out of the flow cell, the valve means are suitably located at the junction of the branched channels, or in one or both of the bead outlet channel and fluid outlet channel, e.g. in the bead outlet channel and fluid outlet channel downstream of the point where the common outlet channel divides, or at the point where the limbs branch off from the stem.

In one embodiment in which the valve means are located at the junction of the branched channels, the valve means may comprise a valve body, having one or more channels therethrough, the channels and the common outlet channel and bead outlet and fluid outlet channels being moveable relative to each other so that the common outlet channel can be brought into communication with either the bead outlet or fluid outlet channels so as to direct a bead along the bead outlet channel.

For example such a valve body may comprise a valve plug having one or more channels passing through it, rotatably moveable within a conforming valve sleeve into which leads the common outlet channel, and out of which lead the bead outlet and fluid outlet channels, and by rotation of the plug within the sleeve the common outlet channel can be brought into communication, via the channels in the plug, with either the bead outlet or fluid outlet channels. Suitably the channel through the plug can be a "Y" shaped plug, allowing entry of fluid into one or other of the limbs or stem of the "Y", and exit of fluid through the stem or another limb and thence into the bead exit channel or the fluid exit channel, rotation of the plug causing a different limb or the stem to be brought into communication with the bead exit channel or the fluid exit channel. Suitable drive means for such a plug will be apparent to those skilled in the art. One suitable drive means is a stepping motor, and stepping motors are commercially available which can provide a suitable degree of rotation of such a plug within a very short time.

In another embodiment the valve means may be located downstream of the point where the common outlet channel branches, for example in one or both of the bead outlet channel and fluid outlet channel. When the valve means are located downstream of the point where the common outlet channel divides it is preferred that the valve means is located close to the point where the channel divides, so that a bead can rapidly travel to a point downstream of the valve. When flow is restricted in one of the channels, for example along a limb in the case of a "Y" channel arrangement, fluid flow is consequently diverted through the other channel. In such a construction, in the first valve configuration the valve means in the fluid outlet channel restricts flow through the fluid outlet channel whilst the valve means in the bead outlet channel allows fluid flow, in the second valve configuration the situation being vice versa, and the valve means may switch from the first to the second configuration when a bead is downstream of the valve in the bead outlet channel. The above described arrangement may use only one valve, for example in a channel arrangement in which flow occurs preferentially along one channel, such as the bead outlet channel, even whilst the other channel, such as the fluid outlet channel, remains open, with a valve means only in the channel of preferential flow. However it is preferred to provide valve means that operate dependently to respectively control flow in both the bead outlet and fluid outlet channels.

In another embodiment the valve means comprise shutters which are reciprocally moveable, e.g. in a direction perpendicular to the flow direction of the bead outlet channel and fluid outlet channel, into respective "closed" and "open" positions in which flow through the channel is restricted, e.g. closed, or is allowed, i.e. the channel is open. With the dimensions of bead outlet channel referred to above, only ca. 1 mm reciprocal movement of the shutter between the closed and open positions is required, facilitating a small device and high speed operation. It is desirable that the shutter moves between the closed and open positions at a high speed, so that a high throughput through the device can be achieved, and so that a minimal quantity of suspension fluid accompanies the beads past the valve means.

Suitably the shutters may be reciprocally moveable pistons, which may be driven mechanically or electromechanically between the closed and open positions. The shutters may be profiled, e.g. with rounded or sloping surfaces, to deflect downstream any beads which are in risk of being caught between the shutter and the wall of the bead outlet channel as the bead closes. Suitable drive means for such shutters will be apparent to those skilled in the art. One suitable drive means is a solenoid, and solenoids are commercially available which can switch in times as short as 2 ms, which is generally faster than needed.

In another embodiment for example, in a branched channel arrangement means may be provided to apply a laterally directed fluidic pulse to a bead as it travels down the common outlet channel to divert the bead into the bead outlet channel. For example in another embodiment the flow of fluid may be diverted into different separate compartments of a moveable slide or rotatable wheel, from which compartments beads may be caused to pass into the bead outlet channel.

In a preferred construction the bead outlet channel is provided with means to introduce a flow of a flushing fluid (which may be the same fluid as the suspension or sheath fluid) upstream of a bead, so that a bead may be flushed along the bead outlet channel. For example when a bead is downstream of the valve means and the valve means closes the channel the bead is in or otherwise restricts flow of fluid through the channel or diverts fluid along another channel, the flow of fluid along the bead outlet channel is restricted. This may inhibit flow of the bead along the bead outlet channel and a flush fluid may therefore assist bead flow downstream of the valve. The flushing fluid introduction means may for example comprise a conduit opening into the bead outlet channel downstream of a valve means, so that via this conduit, when the valve means is in the closed position with a bead downstream relative to the valve means in the bead outlet channel, a flushing fluid may be introduced into the bead outlet channel.

For example the valve means may be provided with a flushing fluid conduit through which flushing fluid may be passed. For example a valve sleeve as described above may be provided with a flushing fluid conduit through which flushing fluid may be introduced, and the valve plug may be rotatable within the valve sleeve into a position in which the flushing fluid channel is brought into communication with the bead outlet channel, via a channel in the plug, to thereby direct flushing fluid into the bead outlet channel. Suitably the plug may include a flushing fluid channel which can be brought into communication with the flushing fluid conduit and the bead exit channel.

Additionally or alternatively a valve means such as a shutter may be provided with an internal conduit which has an opening into the bead outlet channel, via which, a flushing fluid may be introduced into the bead outlet channel, to help the flow of a bead along the channel.

When the bead passes along the bead outlet channel the bulk of suspension and sheath fluid (if used) flow along the fluid outlet channel. This fluid may be directed to a waste disposal receptacle, or alternatively and preferably some or all of the fluid may be recycled to be used as sheath fluid, i.e. by re-introducing the waste fluid into the sheath fluid inlet chamber. It can be desirable to pass such recycled fluid through a filter to catch beads which have inadvertently missed detection and collection and debris such as bead fragments etc. if such is present.

The control means, responsive to a signal from the radiation detector, and capable of directing the valve means as described above, may be any type of electronic control means known to those skilled in the art, and may include data processing means. Typically the signal from detector such as a photodiode or photomultiplier will be an electrical signal. A suitable control means may be a microprocessor or computer, electromechanically linked to the valve drive means. Suitably such a control means may monitor and control other parameters of the device such as the rate of suspension fluid flow, sheath fluid flow and flushing fluid flow etc. The control means may also control the flow of beads into the device, e.g. by controlling the pump, so that only a preferred number of beads, e.g. only one bead, is present in the flow cell at a time. Also the control means may be programmed to overcome the influence of electronic noise, background radiation etc. Typically such a control means, e.g. a microprocessor or computer, can be preprogrammed with such data as the switching time of the valve means, the nature of the change in the radiation detected by the detector occurs as the bead intercepts the incident beam, and the dimensions of the device, in particular the distance between the point where the bead intercepts the incident beam and the entry to the bead outlet channel, and/or the distance between the point where the bead intercepts the incident beam and the valve means in the bead outlet channel, so that the control means can compute the time when the bead is downstream of the valve means in the bead outlet channel and operate the valve means at the correct time, i.e. when the bead is downstream of the valve means. Optimally the control means may direct the valve means such that the valve means is in the first configuration for only the short time necessary for the bead to pass the valve means, so that a minimum quantity of suspension fluid accompanies the bead along the bead outlet channel.

The data processing means may also be made responsive to data relating to the nature of the change in the radiation detected by the detector which occurs as the bead intercepts the incident beam, so that for example if such data indicates that a number of the beads are clumped together the clump may be sent along the fluid outlet channel for disposal. Also for example beads in a sample which show a fluorescent emission may be separated from beads in the sample which do not show a fluorescent emission, and the latter may be diverted along the fluid outlet channel for disposal. Also for example the data processing means may be programmed to differentiate between beads and bubbles passing through the flow cell, for example the construction described above having a radiation obstructer, enables air bubbles and beads to be easily differentiated by the nature of the radiation intensity pulse detected by the detector as the bead or bubble intercepts the beam.

The bead outlet channel may lead to a means for directing individual beads or cohorts of beads into defined locations in a receptacle, for example individual vials, or individual wells in a microtitre plate. This means may comprise for example a tray supporting such vials or a microtitre plate, and a terminal outlet of the bead outlet channel, which are moveable along X-Y axes relative to each other, for example under the control of the control means. Suitable control means and handling robots are known which can impart such X-Y motion to a microtitre well plate.

The device of the invention may be made of conventional materials such as metal, plastics etc., and may conveniently be made in modular form, e.g. with one or more of the bead inlet, sheath chamber, flow cell and valve means in respective interconnectable and exchangeable modules, thereby allowing different selections of such elements to be combined. The device of the invention may be made small, e.g. so that the distance between the bead entry port and the valve means may be a few mm. This small scale allows the device of the invention to work at high throughput. Two or more devices of the invention may be arranged in parallel in arrays, fed by a single reservoir of beads, again to increase throughput of beads.

The device of the invention facilitates rapid and accurate separation and optionally also sorting of beads from a suspension of such beads, and their subsequent deposition into a receptacle with the minimum deposition of accompanying suspension fluid into the receptacle.

BRIEF DESCRIPTION OF THE DRAWINGS

The device will now be described by way of example only with reference to the accompanying drawings, which show:

FIG. 3 Cross and longitudinal sections through flow cells of a device of the invention.

FIG. 4 A schematic cross section of another form of the device.

FIG. 7 A schematic diagram of an alternative device of this invention.

FIGS. 8 and 9 A schematic diagram of the valve means of FIG. 7.

DETAILED DESCRIPTION OF THE DRAWINGS

Figure 1:
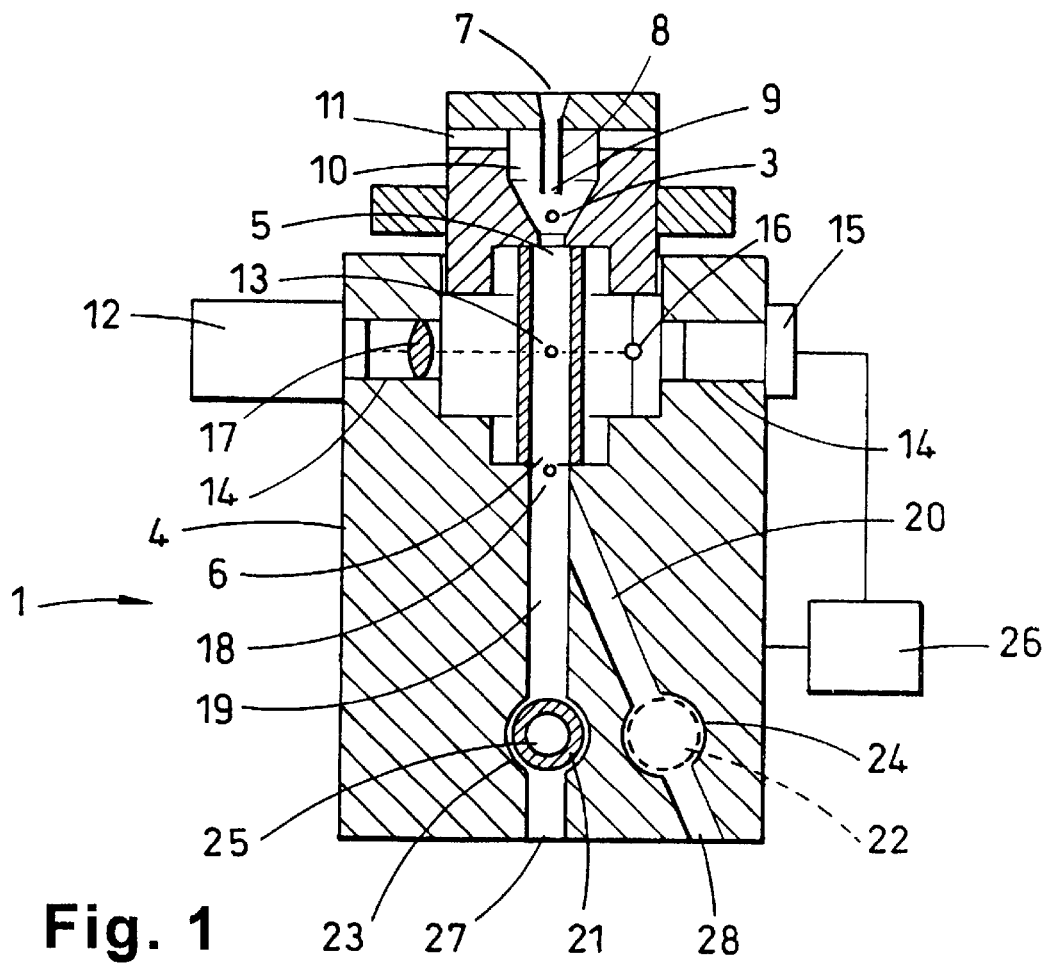
FIG. 1 A schematic longitudinal section through a device of the invention.

Referring to FIGS. 1, 2, 3 and 4 a device 1 (overall) according to this invention is shown. The device comprises a flow cell 2 through which a suspension of polymeric beads 3 ca. 300 microns in diameter, suspended in a suspension fluid such as water or an alcohol such as methanol can flow.

The flow cell 2 is a transparent glass walled narrow tube, of dimensions across the direction of flow of the beads around 800–1000 microns. FIGS. 3A, 3B and 3C show three alternate cross sections for the flow cell, respectively square in external cross section and circular section in internal bore, square in external cross section and square section in internal bore, and circular in external cross section and circular section in internal bore, all three having the flow direction along the longitudinal tube axis. In the device 1 illustrated, the cell 2 is clamped into a body 4 made of metal. The flow cell 2 has an inlet end 5 through which the suspension of beads 3 is introduced in a successive serial flow stream, and the beads 3 flow through the flow cell 2 toward an exit end 6 of the cell 2.

The suspension of beads 3 is introduced into the device 1 illustrated by injection from a source (not shown) connected via a luer connector (not shown) to the device at an inlet port 7. The source may for example be a syringe or a reservoir containing beads suspended in a suspension fluid, and to help keep the beads in suspension there may be a stirrer or other form of agitation in the source. The inlet port 7 communicates with an inlet channel 8 being of cross section comparable to the diameter of the beads 3 and terminating in an orifice 9 of comparable size. Orifice 9 opens into a sheath fluid inlet chamber 10 of wider cross section than the orifice 9, and at its exit end the chamber 10 is in communication with the inlet end 6 of the flow cell 2. The chamber 10 tapers, being cylindrical at its upstream end, narrowing in a conical fashion towards its exit end.

A flow of a sheath fluid is introduced into the chamber 10 upstream of the orifice 9 via inlet 11, so that the beads 3 are carried into the flow cell 2 by the flow of sheath fluid. The sheath fluid helps to even out the flow of beads 3 and assists in achieving suitable serial separation of beads 3.

A radiation source 12 being a laser is located in a position to direct incident radiation (indicated by the dashed line) into the flow cell 2, in an incident direction such that as beads 3 flow through the flow cell 2 they intercept the incident radiation at a point 13, guide apertures 14 being provided in the body 4 for the passage of radiation through the body. The incident direction is substantially normal to the flow direction, with the incident radiation in the form of a narrow beam which is intercepted by the flowing beads 3.

A radiation detector 15, being a photodiode tube, is positioned in line with the incident direction, but on the opposite side of the flow of beads 3 to the laser 12, the square section cell 2 having two opposite facing flat transparent walls, one on either side of the flow of beads. A bead 3 passing between the laser 12 and the detector 15 momentarily eclipses the incident radiation. Between the flow of beads 3 and the detector 15 there is a radiation obstructer 16 which may be in the form of a small opaque sphere, mounted on cross wires, or alternatively can be of the construction more fully shown in FIG. 5, of cross sectional size across the direction of the incident beam, about the same order of magnitude as the incident beam so that incident radiation does not directly impinge upon the detector 15. A lens 17 may optionally be provided to focus deflected light into the detector 15, however the detector 15 may alternatively be positioned close to the flow cell 2 in which case the lens 17 may not be necessary, and is omitted in FIG. 2.

Figure 2:
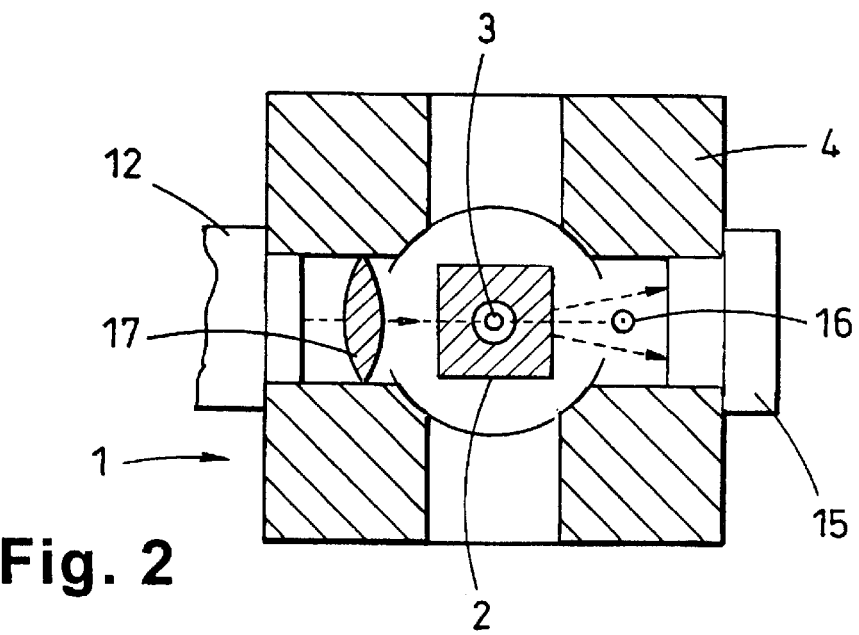
FIG. 2 A schematic cross section through a device of the invention showing the optical path more clearly.

In a convenient form of the construction exemplified by FIG. 2 the distance between the front of the laser 12 and the centre of the flow cell 2 is such that a bead 3 passes ca. 5–7.5 mm, e.g. ca. 6.5 mm in front of the laser 12, and the obstructor 16 is positioned ca. 2.5–5 mm behind the bead 3. These dimensions are found suitable in practice to enable the light to be focused on the bead 3 and to allow sufficient light to be scattered around the obstructor 16 and be collected by the detector 15.

The obstructer 16 as shown in FIG. 3 obstructs the direct entrance of incident radiation into the detector 15, so that when a bead 3 is not present in the flow cell 2 no, or very little incident radiation reaches the detector 15. However, as shown in FIG. 2, when a bead 3 crosses the beam of incident radiation, the radiation is scattered around the bead 3 and reaches the detector 15. This means that a peak of radiation intensity is detected by the detector when a bead crosses the beam.

Downstream from the point 13 where the beads 3 intercept the incident radiation the exit end 6 of the flow cell 2 is in communication with a common outlet channel 18 aligned coaxially in the direction of flow of the beads 3, and which is divided into a "Y" channel arrangement, the common outlet channel 18 comprising the stem of the Y, with flow along the stem toward the fork of the Y. The arms of the Y, downstream of the fork, comprise a bead outlet channel 19 and a fluid outlet channel 20. The limb of the Y which comprises the bead outlet channel 19 is in line with the stem 18 of the Y. The bead outlet channel is around 600–1500 microns across.

Valve means 21, 22 are respectively provided in the bead exit channel 19 and the fluid outlet channel 20. The valve means comprise pistons which are reciprocally moveable in closely conforming valve chambers 23, 24 in a direction perpendicular to the flow direction of the bead outlet channel 19 and fluid outlet channel 20, i.e. being reciprocally in and out of the plane of the drawing.

Piston 21 is shown in a "closed" position in which flow through the bead outlet channel is closed off. Piston 22 is shown dotted, as it is below the plane of the drawing, and is in an "open" position in which flow through the fluid outlet channel is allowed, i.e. the fluid outlet channel is open. This is the "second valve configuration" referred to above, and in this configuration fluid flow is directed through the fluid outlet channel 20 rather than through the bead outlet channel 19. The "first valve configuration" is the opposite, i.e. valve 21 is open and valve 22 is closed, so that fluid flow, and hence beads 3 carried by the flow, is directed through the bead outlet channel 19 rather than through the fluid outlet channel 20.

Piston 21 is provided with an internal conduit 25 which has an opening into the bead outlet channel 19 when the piston 21 is in the open position, by means of which, a flushing fluid (not shown) may be introduced into the bead outlet channel 19, to help the flow of a bead 3 downstream of piston 21 along the channel 19. Alternately the conduit 25 may be absent from piston 21 so that piston 21 is solid, and a conduit 25A may be present, through which a flushing fluid may be introduced when the bead 3 is downstream of the closed valve piston 21, to help the flow of a bead 3 downstream of piston 21 along the channel 19. The conduit 25A is oriented to direct flushing fluid at the piston 21 to dislodge any beads 3 that may be trapped adjacent to the piston 21.

The valves 21, 22 are driven by drive means (not shown) such as solenoids which can move valves 21, 22 reciprocally in and out of the plane of the drawing. The drive means are electromechanically controlled by control means 26, e.g. a computer, electrically linked to detector 15.

The bead outlet channel 19 leads to a terminal outlet 27 by means of which individual beads 3 or cohorts of small numbers of beads 3 may be deposited in individual vials, or individual wells in a microtitre plate (not shown). Excess suspension fluid may be led away to waste from the terminal outlet 28 of the fluid outlet channel 20.

The device 1 works as follows. As a flow of beads 3 in suspension in a suspension fluid is introduced via inlet port 7 it enters chamber 10 where the flow merges with a larger volume of flow of a sheath fluid. By control of the flow rate of the suspension and sheath fluid the beads 3 are caused to be individually serially arranged in the flow of fluid in flow cell 2. Initially valve 22 is open and valve 21 is closed, as shown in FIG. 1.

When a bead 3 intercepts the beam of incident radiation at point 13, a change in the radiation detected by detector 15 occurs. This is communicated electronically to control means 26. From computations based upon parameters of the device 1 such as flow rates and the distance between point 13 and valve 21, the control means 26 directs valve 22 to close and valve 21 to open when the bead 3 is at a point shortly upstream of the fork in the Y of channel 18, so that the flow of fluid and bead 3 is diverted into bead outlet channel 19. When bead 3 is downstream of valve 21, the control means 15 directs valve 21 to close and valve 22 to open, diverting fluid flow along fluid outlet channel 20. The flushing fluid (not shown) is then introduced into the bead outlet channel 19 upstream of the bead 3, to help the flow of a bead 3 along the channel 19 towards terminal outlet 27. In this way only a minimal quantity of fluid accompanies the bead 3 out of outlet 27.

Referring to FIG. 4 another form of the device is shown schematically, parts having a common identity and function to parts in FIGS. 1, 2 and 3 being similarly numbered.

The radiation source 12 is a light emitting diode, suitable for stimulating fluorescence emission from fluorescence labeled beads 3. The radiation detector 15 is positioned at an angle of 90° to the incident direction. The flow cell 2 is again square in section, having two flat transparent wall regions facing the incident direction and the detector 15. The arrangement shown in FIG. 4 is suited for the detection of fluorescence emission from the beads at 90° to the incident direction, and incident radiation does not directly impinge upon the detector 15. The working of the device 1 is otherwise the same as that of the device of FIGS. 1–3. In this way beads 3 in a sample which show a fluorescent emission may be separated from the suspension, or separated from beads in the suspension which do not show a fluorescent emission, the latter being diverted preferentially along the fluid outlet channel 20. Also shown in FIG. 4 is another additional or optional arrangement of radiation detectors 29 and 30. A mirror 31 having an aperture 32 is provided in the line of the incident beam on the opposite side of the bead flow from the source 12. By means of the aperture 32 in the mirror 31 some of the radiation reaches detector 29, and some is deflected by mirror 31 into detector 30. Detectors 29 and 30 may be responsive to different features of the incident beam, e.g. absorbance and light scatter.

Figure 5:
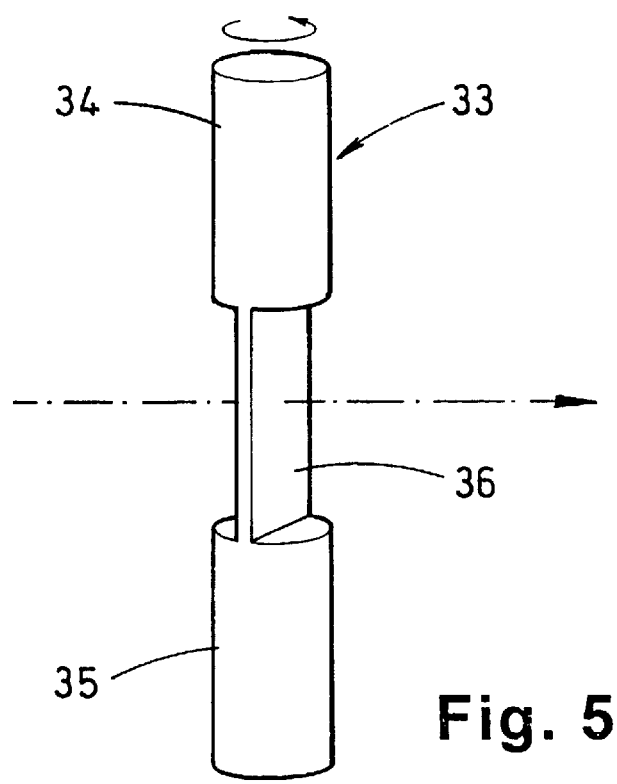
FIG. 5 A schematic view of a construction of radiation obstructer.

Referring to FIG. 5 an alternative form of radiation obstructer is shown, 33 overall. The obstructer 33 comprises a cylindrical rod of opaque material, machined such that its longitudinally terminal ends 34, 35 are cylindrical, but its mid part is in the form of a thin flat strip 36, the width of which is slightly greater than the width of the beam of incident radiation. By rotation of the rod 33 about its longitudinal axis as shown by the arrow, the surface area of the rod 33 exposed to the beam may be varied between the thickness and width of the strip 36. With the dimensions of the optical arrangement of laser 12, cell 2 and detector 15 discussed with reference to FIG. 2 above, suitable dimensions for the cylindrical terminal ends are ca. 1–2, e.g. ca. 1.5 mm diameter, with the width of the strip 36 being correspondingly ca 1.5 mm, its thickness ca 0.1–0.3, e.g. ca. 0.2 mm, and its length ca. 7 mm. An obstructor of these dimensions is found to be suitable to allow sufficient radiation to be scattered into the detector 15.

Figure 6:
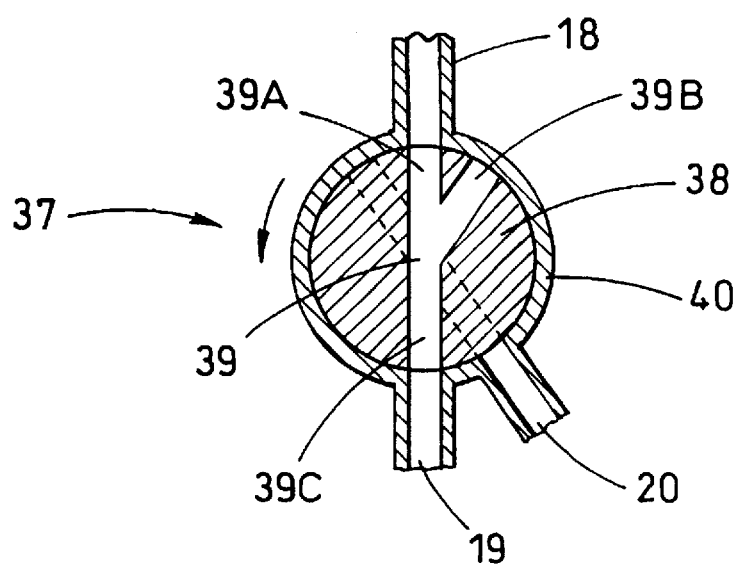
FIG. 6 A cross section through an alternative valve means.

Referring to FIG. 6 an alternative form of valve means is shown overall 37. This comprises a cylindrical valve body 38, having a channel 39 therethrough. The channel 39 is in the form of a "Y" having two branches 39A and 39B and a stem 39C. The body 38 is rotatably moveable within a conforming valve sleeve 40 into which leads the common outlet channel 18, and out of which lead the bead outlet 19 and fluid outlet 20 channels. By rotation of the body 38 within the sleeve 40 the common outlet channel 18 can be brought into communication with either the bead outlet 19 or fluid outlet 20 channel. As shown in FIG. 6, branch 39A is in communication with the common outlet channel 18, bringing the stem 39C into communication with the bead outlet channel 19, i.e. being a first valve configuration. By rotating the body 38 within sleeve 40 in the direction shown by the arrow, as shown by dotted lines branch 39B is in communication with the common outlet channel 18, bringing the stem 39C into communication with the fluid outlet channel 19, i.e. a second valve configuration. Reversal of this rotation returns the valve means to the first configuration.

Referring to FIGS. 7, 8 and 9 an alternative and preferred overall construction of the device of this invention is illustrated. Many of the features of this device are identical to the device of FIG. 1, and parts having a common function and construction are numbered to correspond with FIG. 1.

In the device of FIG. 7, after passing through flow cell 2 and being detected in the same manner as in the device of FIG. 1, beads suspended in a mixture of suspension fluid and sheath fluid are passed to valve means 41 (overall). This comprises a cylindrical valve body 42, which is rotatable in a conforming valve sleeve 43. Valve body 42 has a channel 44 through it. The channel 44 is in the form of a "Y" having two branches 44A and 44B and a stem 44C. The valve sleeve 43 has openings into which leads the common outlet channel 18, and out of which lead the bead outlet 45 and fluid outlet 46 channels. By rotation of the body 42 within the sleeve 43 the common outlet channel 18 can be brought into communication with either the bead outlet 45 or fluid outlet 46 channel. As shown in FIG. 7, branch 44A is in communication with the common outlet channel 18, bringing the stem 44C into communication with the fluid outlet channel 46, i.e. being a second valve configuration. In this configuration fluid can flow through the valve means 41 and out of the fluid outlet channel 46.

The operation of the valve means 41 is shown more clearly in FIGS. 8 and 9. When a bead has been detected by the detector 15, the body 42 is rotated within sleeve 43 in the direction shown by the arrow by means of a stepping motor (not shown) under the control of control means 26. The configuration shown in FIG. 8 is thereby achieved, in which branch 44B is in communication with the common outlet channel 18, bringing the stem 44C into communication with the bead outlet channel 19, i.e. a second valve configuration. With the channel 44 in this configuration a bead 3 enters the channel 44 from the channel 18 and passes through the channel into the bead outlet channel 45, i.e. into the position shown as 3'. When the bead is in position 3' the valve body 42 is rotated back into the second configuration, i.e. in the direction shown by the arrow in FIG. 8, and the position shown in FIG. 9 is achieved. In this position the flow of suspension fluid and sheath fluid is diverted so that it does not flow through the bead outlet channel 45. The valve sleeve is provided with a flushing fluid entry conduit 47, through which flushing fluid may be directed, and the valve body 42 is provided with a flushing channel 48. In the configuration shown in FIG. 9 the flushing channel 48 is in communication both with the flushing fluid entry conduit 47 and the bead outlet channel 45 so that fluid flows through flushing channel 48 and flushes the bead 3 out through bead outlet channel 45.

Excess fluid exiting from fluid outlet channel 46 may be directed to waste, but alternatively may be directed via line 49 back to the sheath fluid chamber 10 via its inlet 11, i.e. recycling the fluid. An in-line filter 50 is provided to remove beads which have inadvertently been missed by the detector, or other debris.

Control 26 also controls the operation of an X–Y movement robot 51 which moves such that a specified microtitre plate well 52 is in a receiving position adjacent the open end of the bead outlet channel 45. In this way the position of each bead 3 can be recorded in a data storage system, and a count of beads may be kept so that all beads are accounted for.

It will be apparent from FIGS. 1 and 7 that the device of the invention may be of modular construction, so that for example different types of detector system modules, e.g. that of FIG. 4 may be combined with different types of valve means modules for particular applications, for example being connected at the outlet 18.

By using a device of the construction described with reference to FIGS. 7, 8 and 9 it was found possible to dispense a single bead in each well of a 96 well microtitre well plate in 6 minutes, and to disperse 10 beads per well in a 96 well plate in 8 minutes, or a single bead per well in a 38 4 well plate in 28 minutes, all with an accuracy of greater than 95%. For example the device took 0.1 seconds to detect a bead, and the valve body could rotate between first and second configurations in 0.07 seconds, 1.25 seconds to dispense a bead, and 2.45 seconds to locate the next well adjacent to the bead outlet channel. It is anticipated that without further inventive effort these latter two times could be reduced to respectively 0.45 and 0.87 seconds, allowing the device to array a bead in each well of a 96 well plate in ca. 1.4 minutes.

What is claimed is:

1. A device for separating polymeric beads from a suspension of a plurality of such beads in a suspension fluid being a liquid, which comprises:
   a flow cell through which a suspension of the beads in the suspension fluid can flow;
   the flow cell having an inlet end through which the suspension of beads may be introduced into the flow cell, such that the beads are arranged in a successive serial flow stream as they flow through the flow cell toward an exit end of the cell;
   a radiation source capable of directing incident radiation into the flow cell in an incident direction such that as beads flow through the flow cell they intercept the incident radiation;
   a radiation detector positioned relative to the radiation source and to the flow of beads such that a change in the radiation detected by the detector occurs as the bead intercepts the incident beam;

a bead outlet channel and a suspension fluid outlet channel located downstream from the point where the beads intercept the incident radiation, and being in communication with the exit end;

valve means which in a first configuration directs suspension fluid flow preferentially through the bead outlet channel rather than through the suspension fluid outlet channel, and alternatively which in a second configuration directs suspension fluid flow preferentially through the suspension fluid outlet channel rather than through the bead outlet channel, so that in the first valve configuration beads are caused to flow through the bead outlet channel;

control means responsive to a signal from the radiation detector resulting from bead intercepting the incident beam, and which directs the valve means into the first valve configuration so that a bead flows through the bead outlet channel, and after the bead is downstream of the valve means then directs the valve means into the second valve configuration;

and wherein the valve means comprise a valve plug, and a conforming valve sleeve into which leads the common outlet channel and out of which lead the bead outlet and fluid outlet channels, the valve plug being rotatably moveable within the valve sleeve, a "Y" shaped channel passing through the valve plug, such that by rotation of the plug within the sleeve the common outlet channel can be brought into communication with the "Y" shaped channel to allow entry of fluid from the common outlet channel into one or other of the limbs or stem of the "Y", and exit of fluid respectively through the stem or another limb and thence into the bead exit channel to thereby provide a first configuration of the valve, and rotation of the plug causing a different limb or the stem to be brought into communication with the bead exit channel or the fluid exit channel, to thereby allow entry of fluid from the common outlet channel into the different limb or stem of the "Y", and exit of fluid through the stem or another limb and thence into the fluid exit channel to thereby provide a first configuration of the valve, the valve sleeve having a flushing fluid conduit through which flushing fluid may be introduced into the valve sleeve from the exterior of the valve sleeve, the valve plug having a flushing fluid channel passing through the plug which by relative rotation of the plug within the sleeve and be brought into contact with both the flushing fluid conduit and the bead outlet channel to thereby direct flushing fluid from the flushing fluid conduit into the bead to thereby direct a bead along the bead outlet channel.

2. Device according to claim 1 characterised in that the flow cell is in the form of a tube of dimensions across the direction of flow of the beads about 1.5–4 times the diameter of the beads.

3. Device according to claim 2 characterized in that a flow of a sheath fluid is introduced around the flow of suspension of beads flowing through the inlet end of the flow cell, the sheath fluid flowing in the same direction as the flow of beads.

4. Device according to claim 1 characterised in that a flow of a sheath fluid is introduced around the flow of suspension of beads flowing through the inlet end of the flow cell, the sheath fluid flowing in the same direction as the flow of beads.

5. Device according to claim 4 characterised in that the suspension fluid and sheath fluid flow through the flow cell in laminar flow.

6. Device according to claim 4 characterised in that upstream of the inlet end of the flow cell, an inlet port for the suspension of beads in suspension fluid is provided, leading to an inlet conduit being of cross section comparable to the diameter of the beads and terminating in an orifice of comparable size which opens into a sheath fluid inlet chamber of wider cross section than the orifice and surrounding the orifice, at its exit end the chamber being in communication with the inlet end of the flow cell.

7. Device according to claim 6 characterized in that the sheath chamber is in the form of a chamber which tapers from a wider upstream end toward a narrower downstream end, being coaxial with the direction of flow through the flow cell, and in communication with the flow cell at its narrow end.

8. Device according to claim 5 characterized in that upstream of the inlet end of the flow cell, an inlet port for the suspension of beads in suspension fluid is provided, leading to an inlet conduit being of cross section comparable to the diameter of the beads and terminating in an orifice of comparable size which opens into a sheath fluid inlet chamber of wider cross section than the orifice and surrounding the orifice, at its exit end the chamber being in communication with the inlet end of the flow cell.

9. Device according to claim 1 characterised in that the incident direction is substantially normal to the flow direction, with the incident radiation in the form of a narrow beam which is intercepted by the flowing beads.

10. Device according to claim 1 characterised in that a radiation detector is positioned relative to the radiation source and to the flow of beads such that the det ec tor is at a non zero angle to the incident direction.

11. Device according to claim 1 characterised in that the radiation detector is positioned relative to the radiation source and to the flow of beads such that the detector is in line with the incident direction, but on the opposite side of the flow of beads to the radiation source.

12. Device according to claim 8 characterised in that between the flow of beads and the detector there is a radiation obstructer of size about the same order of magnitude as the cross section of the incident beam s uch that incident radiation does not directly impinge upon the detector but instead is scattered by beads around the obstructer into the detector.

13. Device according to claim 11 wherein the radiation obstructer is in the form of a strip of opaque material, thin in relation to its width, which may be adjusted by rotation about its longitudinal axis so as to present a surface varying between its width and its thickness to the incident beam.

14. Device according to claim 12 wherein the radiation obstructer is in the form of a strip of opaque material, thin in relation to its width, which may be adjusted by rotation about its longitudinal axis so as to present a surface varying between its width and its thickness to the incident beam.

15. Device according to claim 1 characterised in that the exit end of the flow cell is in communication with a common outlet channel aligned in the direction of flow of the beads, and which divides at a downstream point into two or more channels, being respectively a bead outlet channel and a fluid outlet channel.

16. Device according to claim 1 characterised in that the valve means comprise a valve body, having one or more channels therethrough, the channels and the common outlet channel and bead outlet and fluid outlet channels being moveable relative to each other so that the common outlet channel can be brought into communication with either the bead outlet or fluid outl et channels so as to direct a bead along the bead outlet channel.

17. Device according to claim 16 characterized in that the bead outlet channel is provided with means to introduce a flow of a flushing fluid upstream of a bead, so that a bead may be flushed along the bead outlet channel.

18. Device according to claim 1 characterized in that the valve means comprise shutters situated adjacent the bead outlet channel and fluid outlet channel which are reciprocally moveable into respective "closed" and "open" positions in which flow through the bead outlet channel and fluid outlet channel is respectively restricted or is allowed.

19. Device according to claim 18 characterized in that the bead outlet channel is provided with means to introduce a flow of a flushing fluid upstream of a bead, so that a bead may be flushed along the bead outlet channel.

20. Device according to claim 15 characterized in that the bead outlet channel is provided with means to introduce a flow of a flushing fluid upstream of a bead, so that a bead may be flushed along the bead outlet channel.

21. Device according to claim 1, characterised in that fluid from the fluid exit channel is recycled back to the sheath fluid chamber.

22. A device according to claim 1 wherein the flushing fluid is directed into the bead outlet channel whilst the valve means is in its second configuration, and in this second configuration the flow of suspension fluid through the bead outlet channel is closed.

23. Device according to claim 22 characterized in that a flow of a sheath fluid is introduced around the flow of suspension of beads flowing through the inlet end of the flow cell, the sheath fluid flowing in the same direction as the flow of beads.

24. Device according to claim 22 characterized in that the flow cell is in the form of a tube of dimensions across the direction of flow of the beads about 1.5–4 times the diameter of the beads.

25. Device according to claim 22 characterized in that the radiation detector is positioned relative to the radiation source and to the flow of beads such that the detector is in line with the incident direction, but on the opposite side of the flow of beads to the radiation source.

26. A device for separating polymeric beads from a suspension of a plurality of such beads in a fluid being a liquid, which comprises:

a flow cell through which a suspension of the beads in the fluid can flow;

the flow cell having an inlet end through which the suspension of beads may be introduced into the flow cell, such that the beads are arranged in a successive serial flow stream as they flow through the flow cell toward an exit end of the cell;

a radiation source capable of directing incident radiation into the flow cell in an incident direction such that as beads flow through the flow cell they intercept the incident radiation;

a radiation detector positioned relative to the radiation source and to the flow of beads such that a change in the radiation detected by the detector occurs as the bead intercepts the incident beam;

a bead outlet channel and a fluid outlet channel located downstream from the point where the beads intercept the incident radiation, and being in communication with the exit end;

valve means which in a first configuration directs fluid flow preferentially through the bead outlet channel rather than through the fluid outlet channel, and alternatively which in a second configuration directs fluid flow preferentially through the fluid outlet channel rather than through the bead outlet channel, so that in the first valve configuration beads are caused to flow through the bead outlet channel;

control means responsive to a signal from the radiation detector resulting from bead intercepting the incident beam, and which directs the valve means into the first valve configuration so that a bead flows through the bead outlet channel, and after the bead is downstream of the valve means then directs the valve means into the second valve configuration;

and wherein the radiation detector is positioned relative to the radiation source and to the flow of beads such that the detector is in line with the incident direction, but on the opposite side of the flow of beads to the radiation source, and between the flow of beads and the detector there is a radiation obstructer of size about the same order of magnitude as the cross section of the incident beam such that incident radiation does not directly impinge upon the detector but instead is scattered by beads around the obstructer into the detector, and wherein the radiation obstructer is in the form of a strip of opaque material, thin in relation to its width, which may be adjusted by rotation about its longitudinal axis so as to present a surface varying between its width and its thickness to the incident beam.

27. Device according to claim 26 characterized in that the flow cell is in the form of a tube of dimensions across the direction of flow of the beads about 1.5–4 times the diameter of the beads.

28. Device according to claim 26 characterized in that a flow of a sheath fluid is introduced around the flow of suspension of beads flowing through the inlet end of the flow cell, the sheath fluid flowing in the same direction as the flow of beads.

29. Device according to claim 26 characterized in that the exit end of the flow cell is in communication with a common outlet channel aligned in the direction of flow of the beads, and which divides at a downstream point into two or more channels, being respectively a bead outlet channel and a fluid outlet channel.

30. Device according to claim 26 characterized in that the valve means comprise a valve body, having one or more channels therethrough, the channels and the common outlet channel and bead outlet and fluid outlet channels being moveable relative to each other so that the common outlet channel can be brought into communication with either the bead outlet or fluid outlet channels so as to direct a bead along the bead outlet channel.

31. Device according to claim 26 characterized in that the valve means comprise shutters situated adjacent the bead outlet channel and fluid outlet channel which are reciprocally moveable into respective "closed" and "open" positions in which flow through the bead outlet channel and fluid outlet channel is respectively restricted or is allowed.

32. Device according to claim 26 characterized in that the bead outlet channel is provided with means to introduce a flow of a flushing fluid upstream of a bead, so that a bead may be flushed along the bead outlet channel.

* * * * *